United States Patent [19]

Vanlautem et al.

[11] Patent Number: 4,705,604

[45] Date of Patent: Nov. 10, 1987

[54] PROCESS FOR EXTRACTING POLY-BETA-HYDROXYBUTYRATES BY MEANS OF A SOLVENT FROM AN AQUEOUS SUSPENSION OF MICROORGANISMS

[75] Inventors: Noël Vanlautem, Wavre; Jacques Gilain, Brussels, both of Belgium

[73] Assignee: Solvay & Cie. (Société Anonyme), Brussels, Belgium

[21] Appl. No.: 746,381

[22] Filed: Jun. 19, 1985

[30] Foreign Application Priority Data

Jul. 6, 1984 [FR] France ................................ 84 10921

[51] Int. Cl.[4] ........................ B01D 3/36; C07C 69/66; C08G 63/06

[52] U.S. Cl. ........................................ 203/67; 203/14; 203/43; 435/146; 435/135; 528/361; 528/491; 528/501; 560/185

[58] Field of Search ........................ 203/14, 67, 43–46; 528/361, 491, 501, 502, 498; 435/146; 560/185; 562/579

[56] References Cited

U.S. PATENT DOCUMENTS

| | | | |
|---|---|---|---|
| 1,934,677 | 11/1933 | Ash | 203/14 |
| 2,602,045 | 7/1952 | Hodge | 203/14 |
| 3,402,107 | 9/1968 | Seeliger et al. | 203/14 |
| 3,687,819 | 8/1972 | Levin | 203/14 |
| 4,197,166 | 4/1980 | Inoue et al. | 203/14 |
| 4,310,684 | 1/1982 | Vanlautem et al. | 528/361 |
| 4,365,088 | 12/1982 | Vanlautem et al. | 562/579 |
| 4,562,245 | 12/1985 | Stageman | 528/361 |

FOREIGN PATENT DOCUMENTS

| | | | |
|---|---|---|---|
| 0014490 | 8/1980 | European Pat. Off. . | |
| 0036699 | 9/1981 | European Pat. Off. . | |
| 46017 | 2/1982 | European Pat. Off. . | |
| 58480 | 8/1982 | European Pat. Off. . | |
| 0124309 | 11/1984 | European Pat. Off. . | |
| 2486072 | 1/1984 | France . | |
| 2120671 | 5/1982 | United Kingdom | 528/361 |

*Primary Examiner*—Wilbur Bascomb
*Attorney, Agent, or Firm*—Spencer & Frank

[57] ABSTRACT

A process for extracting poly-beta-hydroxybutyrates from an aqueous suspension of microorganisms, in which an azeotropic distillation, and an extraction of the polymer by means of the solvent used, are carried out simultaneously.

The poly-beta-hydroxybutyrates obtained can be used in medicine.

12 Claims, No Drawings

PROCESS FOR EXTRACTING POLY-BETA-HYDROXYBUTYRATES BY MEANS OF A SOLVENT FROM AN AQUEOUS SUSPENSION OF MICROORGANISMS

BACKGROUND OF THE INVENTION

1. Field of the Invention

The present invention relates to a process for extracting poly-beta-hydroxybutyrates from an aqueous suspension of microorganisms, in which an azeotropic distillation, coupled to an extraction by solvent, is carried out.

2. Background of the Art

Many microorganisms are capable of synthesising poly-beta-hydroxybutyrates, the main function of which in these microorganisms appears to be the storage of energy in the form of carbon-containing material. These poly-beta-hydroxybutyrates (PHB) constitute a raw material which is of value from the industrial standpoint. Many techniques have already been envisaged to separate them from the biomass.

Thus, it was already proposed in Patent Application EP-A No. 0,015,123 to dry the bacterial cells by introducing a hot gas in a first stage, and then, after cooling in a second stage, to extract the poly-beta-hydroxybutyrates with a suitable solvent. To this two-stage process, supplementary stages may be added such as, in particular, a stage in which the bacterial cells are lysed before extraction with the solvent.

Another process is described in Patent Application EP-A No. 0,046,017. According to this document, the bacterial cells are flocculated at a high temperature by modifying the pH in a first stage, and then, in a second stage, after cooling, the suspension of flocculated bacterial cells is heated by introducing water vapour under pressure; this operation is followed or preceded by an additional modification of the pH. The flocculated cells are then dried so as to obtain a porous granular product, for the purpose of subsequent contact with the solvent for extraction of the PHB.

In Patent Application EP-A No. 0,058,480, another process requiring several stages has been described. According to this process, the bacterial culture is first dried by spraying at a high temperature, and the dried cells, after being cooled, are then brought into contact with methanol for the purpose of extracting the lipids, and finally with a solvent for the purpose of extracting the poly-beta-hydroxybutyrates. The solution is then further cooled below 0° C., and then heated to 20° C. for 30 minutes, a gel thereby being obtained. This gel is subjected to pressure for the purpose of expelling the solvent.

The processes of the prior art nevertheless have disadvantages when they are carried out in industrial installations, on account of the complexity imposed on the installations and the high energy expenditure resulting from the successive heating and cooling.

SUMMARY OF THE INVENTION

The present invention relates to the provision of a process for extracting poly-beta-hydroxybutyrates which does not have the disadvantages of the earlier processes.

To this end, the present invention relates to a process for extracting poly-beta-hydroxybutyrates by means of a solvent from an aqueous suspension of microorganisms, characterised in that (a) a solvent for poly-beta-hydroxybutyrates is chosen which forms a minimum boiling azeotropic mixture with water, (b) the water is removed by azeotropic distillation, and (c) the extraction is carried out at least partially at the boiling point of the azeotropic mixture.

By the term "solvent which forms a minimum boiling azeotropic mixture with water", is intended to mean a solvent which, when mixed with water, forms a mixture the boiling point of which is constant and is less than the boiling point of the solvent or water taken separately, and which retains a constant composition at a given pressure [Encyclopédie internationale des Sciences et des Tehcniques—Larousse (1970, Vol. 2, p. 205–206)].

As a solvent for poly-beta-hydroxybutyrates which forms a minimum boiling azeotropic mixture with water, any solvent having this property can be used. The solvents are usually chosen from organic solvents, and more especially from halogenated aliphatic solvents. Among the latter, chlorinated saturated aliphatic solvents are generally employed.

Good results were obtained with chloromethanes, chloroethanes and chloropropanes. Among the latter, 1,2-dichloroethane, 1,1,2-trichloroethane and 1,2-dichloropropane are preferably employed.

1,2-Dichloroethane is most especially preferred as a solvent for poly-beta-hydroxybutyrates which forms an azeotropic mixture with water.

For information, the boiling points of solvents which have given good results, and also the boiling point of the minimum azeotropic mixture, at atmospheric pressure, formed by the solvents with water, are given in the Table below.

TABLE

| | (P = 1.0 bar) | |
|---|---|---|
| Solvent | Boiling point °C. | Azeotropic mixture with water °C. |
| 1,1,2-trichloroethane | 113.7 | 86.0 |
| 1,2-dichloroethane | 83 | 72.0 |
| 1,2-dichloropropane | 96 | 78 |

The aqueous suspensions of microorganisms which can be treated according to the invention can be obtained from microorganisms of various origins. The selection of the microorganisms is generally made on the basis of the relative amount of poly-beta-hydroxybutyrates present in the microorganism, and also according to the rate of growth of the microorganism and its rate of synthesis of polybeta-hydroxybutyrates.

The microorganisms can be treated directly by the extraction solvent in their culture medium. It is, however, also possible to use aqueous suspensions of microorganisms resulting from partial separation of the microorganisms from their culture medium prior to the extraction. This partial separation can be accomplished by any means known for this purpose. The culture can be centrifuged or ultrafiltered for the purpose of being concentrated, and this can be followed or otherwise by one or more washes for the purpose of removing a fraction of the residues of the nutrient medium. The process of the invention also applies to aqueous suspensions of microorganisms originating from the resuspension in water of pre-dried cultures. It is, however, clear that such a technique is not preferred, on account of the additional energy expenditure involved therein.

The ratio between the amount of the aqueous suspension of microorganisms used and the extraction solvent used is not in itself critical. Ratios by weight of between 1:1 and 1:100 are generally employed. Ratios between 1:2 and 1:50 are customarily used, and finally working ratios of between 1:5 and 1:20 are preferably employed.

The choice of this ratio is influenced by various parameters, such as the nature of the microorganisms to be treated, the temperature, the number of extractions and the yield desired by extraction. Furthermore, the removal of the cell residues is easier when there are fewer microorganisms in the extraction medium.

The pressure at which the process is carried out is not critical, and is generally between 0.1 and 10 bar.

In the process of the invention, the water is removed by azeotropic drying. The removal of the water takes place until a phase of an anhydrous solvent or of a solvent still saturated with water is obtained; and this results in a single clear liquid extract phase being obtained which contains the poly-beta-hydroxybutyrates.

The process can be carried out in any apparatus designed for this purpose. The process according to the invention can be carried out continuously or discontinuously, with the aqueous suspensions of microorganisms and extraction solvents circulating in the same direction or in opposite directions.

In the process according to the invention, the solvent, saturated with water or otherwise, resulting from the azeotropic distillation can optionally be recycled as an extraction solvent.

After extraction, the solvent containing the poly-beta-hydroxybutyrates can be freed of compounds insoluble in the medium, such as the cell membranes of microorganisms. For this purpose, any known means can be used. This operation is customarily accomplished by means of one or more filtrations.

The extracted poly-beta-hydroxybutyrates can be separated from the extraction solvent by any method known for this purpose. Thus, they can be separated by evaporation of the solvent, or else by simply adding a precipitating agent. As precipitating agents which can be used, mention can be made of compounds which are not solvents of poly-beta-hydroxybutyrates, such as petroleum ether, unsubstituted aliphatic hydrocarbons, aromatic compounds including benzene, or aliphatic alcohols. Preferred precipitating agents are aliphatic alcohols and ketones, and more especially, for economic reasons, methanol and ethanol.

The poly-beta-hydroxybutyrates separated from the extraction solvent can then be purified by one or more washes with non-solvents such as those mentioned above, and dried, after which they take the form of a white mass. The recovery and purification operations are customarily carried out at room temperature.

Poly-beta-hydroxybutyrates are polymers which have many applications, in particular in surgery where they can be used in the form of threads, since they can be readily sterilised. Furthermore, these polymers can be shaped by the various known techniques of moulding to make prostheses. They can also be spun or extruded by the customary methods. Finally, these poly-beta-hydroxybutyrates can be depolymerised in the form of oligomers, or even in the form of the monomer which is beta-hydroxybutyric acid. To this end, it is possible to use, in particular, methods such as that described in Patent Application FR-A-2,486,072.

DESCRIPTION OF THE PREFERRED EMBODIMENTS

The examples which follow serve to illustrate the invention.

EXAMPLE 1

In a 2-l round-bottomed flask equipped with a stirrer, a thermometer, a dropping funnel and a water-cooled condenser, there are introduced 79.5 g of an aqueous suspension of microorganisms consisting of a bacterial culture of the strain *Alcaligenes eutrophus* containing 53 g of dry matter.

1 l of 1,2-dichloroethane is then introduced. With efficient stirring, the suspension is brought to reflux at atmospheric pressure in the course of 0.4 h. At 72° C., the water/1,2-dichloroethane minimum boiling azeotropic mixture is removed in 1.5 h. The organic solvent is recycled during this distillation.

When all the water has been removed in the form of an azeotropic mixture, the temperature reaches 83° C., and this temperature is maintained for 0.5 h.

The suspension is then rapidly cooled, and then filtered under pressure at 3 bar in order to remove the solid remains of the microorganisms. The cake is washed with 300 ml of 1,2-dichloroethane.

The organic solution is then evaporated to dryness, and 29.15 g of poly-beta-hydroxybutyrates are recovered.

The yield of the extraction is given by the weight of the extracted polymer over the weight of dry matter of the microorganisms used, and amounts to 55%.

EXAMPLES 2 AND 3

Example 1 is repeated, using 106 g of an aqueous suspension of microorganisms containing 53 g of dry matter.

The azeotropic entrainment of the water at 72° C. takes 1.6 h.

After this, the temperature of 83° C. is maintained, in a first instance (Example 2) for 0.4 h, and in a second instance (Example 3) for 1.4 h.

The respective recoveries of poly-beta-hydroxybutyrates are 28.6 g (Example 2) and 30.0 g (Example 3) [which corresponds to extraction yields of, respectively, 54% (Example 2) and 56% (Example 3)].

From these results, it can be deduced that the invention enables optimum extraction yields of poly-beta-hydroxybutyrates to be obtained by an integrated process in which a drying procedure by forming an azeotropic mixture is coupled to an actual extraction procedure.

What is claimed is:

1. A solvent extraction process for extracting poly-beta-hydroxybutrates from an aqueous suspension of micro-organisms containing poly-beta-hydroxybutrates, the process comprising:

(a) contacting the aqueous suspension of micro-organisms with a selected extraction solvent for poly-beta-hydroxybutyrates, which extraction solvent forms a minimum boiling azeotropic mixture with water, and which azeotropic mixture has an azeotropic boiling point;

(b) removing water from the aqueous suspension of micro-organisms by azeotropic distillation of the azeotropic mixture at the azeotropic boiling point; and (c) simultaneously extracting the poly-beta-hydroxybutyrates with the extraction solvent at the azeotropic boiling point of the azeotropic mixture to obtain an extract phase containing poly-beta-hydroxybutyrates and extraction solvent.

2. The process according to claim 1, wherein the extraction solvent is a halogenated aliphatic solvent.

3. The process according to claim 1, wherein the extraction sovlent is a chorinated saturated aliphatic solvent.

4. The process according to claim 3, wherein the extraction solvent is selected from the group consisting of chloromethanes, chloroethanes and chloropropanes.

5. The process according to claim 4, wherein the extraction solvent is 1,2-dichloroethane.

6. The process according to claim 1, wherein the water is removed azeotropically until an anhydrous extract phase containing the poly-beta-hydroxybutyrates and extraction solvent is obtained.

7. The process according to claim 1, wherein the water is removed azeotropically until the extraction solvent in the extract phase is saturated with water at the azeotropic boiling point.

8. The process according to claim 1, wherein the aqueous suspension of micro-organisms and the extraction solvent are present in ratios by weight ranging from 1:2 to 1:50.

9. The process according to claim 8, wherein the ratios by weight range from 1:5 to 1:20.

10. The process according to claim 1, wherein the aqueous suspension of micro-organisms is obtained from a culture medium, includes the culture medium, and is contacted by the selected extraction solvent directly without any intervening steps.

11. The process according to claim 1, wherein the aqueous suspension of micro-organisms is obtained from a culture medium, is the result of a process consisting essentially of separating the micro-organisms from at least a portion of the culture medium, and is contacted by the extraction solvent directly without any intervening steps.

12. The process according to claim 1, wherein the aqueous suspension of micro-organisms is obtained from a culture medium, is the result of a process consisting essentially of separating the micro-organisms from at least a portion of the culture medium to form a separated product containing the micro-organisms, drying the separated product, and resuspending the dried, separated product in water.

* * * * *